(12) United States Patent
Ronen et al.

(10) Patent No.: US 11,529,068 B2
(45) Date of Patent: Dec. 20, 2022

(54) IMPEDANCE MEASUREMENT

(71) Applicant: Sensible Medical Innovations Ltd., Kfar Neter (IL)

(72) Inventors: Amir Ronen, Ramot Menashe (IL); Shlomi Bergida, Udim (IL)

(73) Assignee: Sensible Medical Innovations Ltd., Netanya (IL)

( * ) Notice: Subject to any disclaimer, the term of this patent is extended or adjusted under 35 U.S.C. 154(b) by 0 days.

(21) Appl. No.: 16/301,750

(22) PCT Filed: May 15, 2017

(86) PCT No.: PCT/IL2017/050540
§ 371 (c)(1),
(2) Date: Nov. 15, 2018

(87) PCT Pub. No.: WO2017/119243
PCT Pub. Date: Nov. 23, 2017

(65) Prior Publication Data
US 2019/0336036 A1  Nov. 7, 2019

Related U.S. Application Data

(60) Provisional application No. 62/336,665, filed on May 15, 2016.

(51) Int. Cl.
*A61B 5/085* (2006.01)
*A61B 5/0538* (2021.01)
*A61B 5/00* (2006.01)

(52) U.S. Cl.
CPC ............ *A61B 5/0538* (2013.01); *A61B 5/085* (2013.01); *A61B 5/6804* (2013.01);
(Continued)

(58) Field of Classification Search
CPC .......... A61B 5/6847; A61B 5/085; A61B 2560/0228; A61B 5/6833; A61B 5/6804; A61B 5/0538
See application file for complete search history.

(56) References Cited

U.S. PATENT DOCUMENTS

| 6,332,870 B1 * | 12/2001 | Van Den Berg | A61B 5/027 600/504 |
| 2004/0105574 A1 * | 6/2004 | Pfaff | G06T 19/00 382/128 |

(Continued)

FOREIGN PATENT DOCUMENTS

| CN | 103930021 | 7/2014 |
| EP | 2752158 | 7/2014 |
| WO | WO 2017/199243 | 11/2017 |

OTHER PUBLICATIONS

Schneider, A., Hommel, G., & Blettner, M. (2010). Linear regression analysis: part 14 of a series on evaluation of scientific publications. Deutsches Arzteblatt international, 107(44), 776-782. doi:10.3238/arztebl.2010.0776 (Year: 2010).*

(Continued)

*Primary Examiner* — Daniel L Cerioni

(57) ABSTRACT

A system comprising a plurality of electrodes adapted to measure bio impedance measurements using electrical currents passing in a target thorax area of a target therebetween during a learning phase, at least one radiofrequency (RF) sensor adapted to measure RF interaction measurements of RF radiation interacting with the target thorax area during the learning phase, and at least one processor adapted to: calculate calibration function according to the bio impedance measurements and the RF interaction measurements, and determine a target thorax area value by adjusting subsequent bio impedance measurements using subsequent
(Continued)

electrical currents passing in the target thorax area during an operational learning phase using the calibration function.

11 Claims, 2 Drawing Sheets

(52) U.S. Cl.
CPC .......... *A61B 5/6833* (2013.01); *A61B 5/6847* (2013.01); *A61B 2560/0228* (2013.01)

(56) References Cited

U.S. PATENT DOCUMENTS

| | | | |
|---|---|---|---|
| 2006/0241513 A1* | 10/2006 | Hatlestad | A61B 5/0809 600/547 |
| 2009/0278685 A1* | 11/2009 | Potyrailo | G01N 33/0073 340/572.1 |
| 2010/0056907 A1* | 3/2010 | Rappaport | A61B 5/05 600/425 |
| 2010/0168530 A1* | 7/2010 | Chetham | A61B 5/0537 600/301 |
| 2010/0256462 A1* | 10/2010 | Rappaport | A61B 5/00 600/301 |
| 2011/0025295 A1* | 2/2011 | Saroka | G01R 35/005 324/72 |
| 2011/0319746 A1* | 12/2011 | Kochba | A61B 5/4848 600/407 |
| 2012/0041279 A1* | 2/2012 | Freeman | A61B 5/053 600/301 |
| 2013/0060103 A1* | 3/2013 | Bergida | A61B 5/0031 600/302 |
| 2013/0225989 A1* | 8/2013 | Saroka | A61B 5/0064 600/430 |
| 2014/0378812 A1* | 12/2014 | Saroka | A61B 5/0507 600/407 |
| 2014/0378813 A1* | 12/2014 | Saroka | A61B 5/0507 600/407 |
| 2015/0031979 A1* | 1/2015 | Rappaport | A61B 5/0806 600/407 |
| 2015/0133763 A1* | 5/2015 | Saroka | A61B 5/05 600/407 |
| 2016/0095532 A1* | 4/2016 | Weinberg | A61B 5/7207 600/422 |
| 2016/0095534 A1* | 4/2016 | Thakur | A61B 5/4842 600/547 |
| 2019/0282164 A1* | 9/2019 | Saroka | A61B 5/6823 |

OTHER PUBLICATIONS

Supplementary European Search Report and the European Search Opinion dated Apr. 18, 2019 From the European Patent Office Re. Application No. 17798879.7. (7 Pages).
International Preliminary Report on Patentability dated Nov. 29, 2018 From the International Bureau of WIPO Re. Application No. PCT/IL2017/050540. (5 Pages).
International Search Report and the Written Opinion dated Aug. 24, 2017 From the International Searching Authority Re. Application No. PCT/IL2017/050540. (10 Pages).
Notification of Office Action and Search Report dated Oct. 27, 2021 From the State Intellectual Property Office of the People's Republic of China Re. Application No. 201780043677.5. (6 Pages).
Office Action dated Oct. 17, 2021 From the Israel Patent Office Re. Application No. 263064. (3 Pages).

\* cited by examiner

IMPEDANCE MEASUREMENT

RELATED APPLICATIONS

This application is a National Phase of PCT Patent Application No. PCT/IL2017/050540 having International filing date of May 15, 2017, which claims the benefit of priority under 35 USC § 119(e) of U.S. Provisional Patent Application No. 62/336,665 filed on May 15, 2016. The contents of the above applications are all incorporated by reference as if fully set forth herein in their entirety.

BACKGROUND

Bio impedance measurements are known to be used to monitor fluid content in a subject's thorax.

Some bio impedance measurement implementations suggest using implanted electrodes. For example, bio impedance measurement is utilized in some pacemakers, where the bio impedance associated with tissues/organs located in-between the pacemaker electrodes and/or case is measured. For example, Medtronic Plc of Dublin Ireland offers OptiVol®, which provides fluid status monitoring through intrathoracic impedance measurements. OptiVol® Fluid Status Monitoring is utilized with implantable cardioverter defibrillator (ICD) or cardiac resynchronization therapy device (CRT-D). External devices, which are able to perform Bio impedance measurements, are also used, for example the Zoe fluid status monitor from NMT medical. The electrical principle behind bio impedance is Ohm's law. When a sinusoidal electrical current passes through a medium, a sinusoidal voltage drop in magnitude is generated. The electrical resistance gives the relationship between the electrical current and the corresponding voltage. An electrical current that passes through biological tissue is impeded by biological tissue resistance, which causes a phase shift between the sinusoidal electrical current and the sinusoidal voltage. Therefore, the tissue impedance that is calculated depends on both the magnitude of the signal and the phase shift that is generated. Depending on the frequencies that are used, different parameters can be measured within the body. High frequency signals are able to pass through the cell membrane and as a consequence both the intracellular and extracellular impedance is measured. Low frequency signals on the other hand only measure the impedance of the extracellular compartment. These properties can be used to measure different parameters. Depending on the desired output, two different bio impedance measuring techniques can be distinguished, i.e. single-frequency measurements and multi-frequency measurements. Multi-frequency measurements, also known as bio impedance spectroscopy (BIS), employ electrical currents of multiple frequencies through the body and can be used to determine static parameters (e.g. body composition, fluid status, etc.). Single-frequency signals on the contrary, can be used to measure more dynamic parameters, such as respiration (2). Single-frequency bio impedance devices that measure respiration can be used in patients suffering from pulmonary problems such as chronic obstructive pulmonary disease, sleep apnea or asthma.

Bio impedance technology has limitations due to the use of electrical currents for the measurements, causing accuracy, specificity and stability issues limiting the use of bio-impedance in relative and trend analysis.

SUMMARY

According to some embodiments of the present invention, there is provided a system. The system comprises a plurality of electrodes adapted to measure bio impedance measurements using electrical currents passing in a target thorax area of a target therebetween during a learning phase, at least one radiofrequency (RF) sensor adapted to measure RF interaction measurements of RF radiation interacting with the target thorax area during the learning phase. The processor (s) are adapted to calculate calibration function according to the bio impedance measurements and the RF interaction measurements and determine a target thorax area value by adjusting subsequent bio impedance measurements using subsequent electrical currents passing in the target thorax area during an operational learning phase using the calibration function.

Optionally, the system comprises the RF interaction measurements and the bio impedance measurements are a sequence of pairs of time correlated measurements, each the pair comprises one of the RF interaction measurements and one of the bio impedance measurements; wherein the calibration function is calculated according to the sequence of pairs.

More optionally, the pairs are taken during different times when different fluid levels are found in the target thorax area.

Optionally, the system comprises the target thorax area is a lungs area.

Optionally, the system comprises the calibration function is selected from a group consisting of a linear model, a logarithmic model, a logistic model, a sigmoid model and a generalized logistic function.

Optionally, the system comprises the calibration function is adapted according to at least one anatomical parameter of the target.

Optionally, the system comprises the calibration function is adapted according to at least one physiological parameter of the target.

According to some embodiments of the present invention, there is provided a method of determining a target thorax area value. The method comprises calculating calibration function according to bio impedance measurements using electrical currents passing in a target thorax area during a learning phase and RF interaction measurements of RF radiation interacting with the target thorax area during the learning phase and determining a target thorax area value of the target thorax area according to an adjustment of subsequent bio impedance measurements using subsequent electrical currents passing in the target thorax area during an operational phase by the calibration function.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description In the drawings.

DETAILED DESCRIPTION

Figure 1:
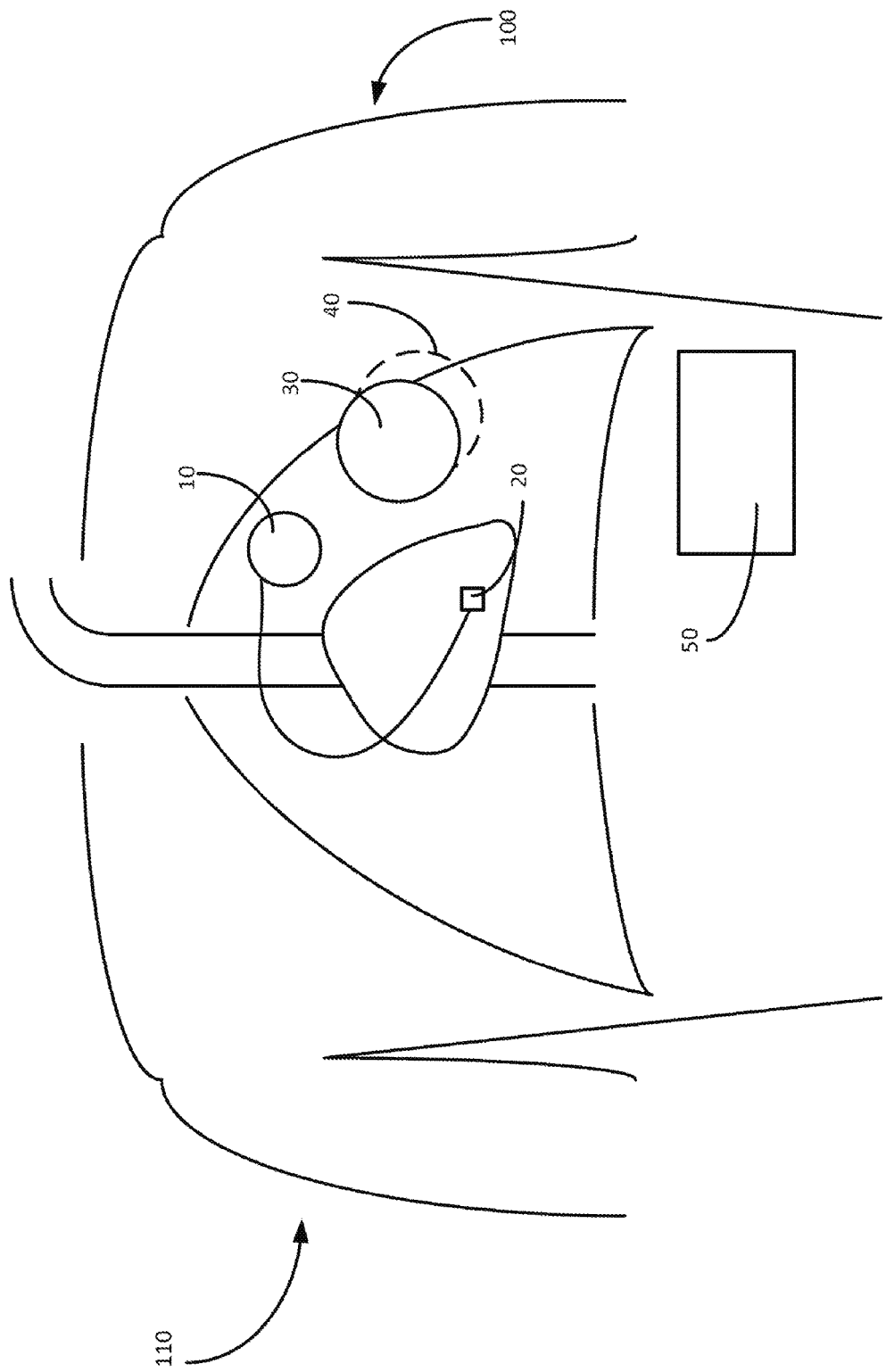
FIG. 1 is a schematic illustration of a bio impedance measuring device worn on an exemplary subject and adapted to determine target thorax area values based on a calibration function calculated according to readings of an RF sensor, according to some embodiments of the present invention.

There is provided in accordance with an aspect of the presently disclosed subject matter a device that is capable of determining a fluid level in the subject's thorax.

According to examples of the presently disclosed subject matter, there are provided methods and devices for using a calibration function calculated based on RF measurements and bio impedance measurements for adjusting subsequent bio impedance measurements in the process of calculating thorax area values such as fluid level values. The calibration function is optionally used in a bio impedance measuring device, for example implanted and/or wearable bio impedance measuring device based on a calibration function calculated according to bio impedance measurements and signals acquired using an RF sensor comprising radiofrequency (RF) signal generator and signal analyzer system. The impedance measuring device may include one or more electrodes and RF signal generator (e.g. RF transceiver that includes EF antenna(s)) and a processing unit, for example one or more processors for computing the bio impedance values and the calibration function. The impedance values may be obtained from impedance level measurement(s) acquired from electrical current(s) passing between at least the electrodes of the pair. Optionally, the calibration function is set to adjust subsequent impedance level measurement(s) for the calculation of thorax area values. The impedance level measurement(s) may be indicative of fluid content in the subject's thorax and/or fluid content change in the subject's thorax. The RF sensor provides an RF interaction measurement(s), for example interception(s) of RF radiation reflected or passing through the subject's thorax after interacting with the subject's body. Optionally, a sequence of pairs of measurements is gathered during a learning phase. Each pair includes an RF measurement and a bio impedance measurement which are correlated with one another, for instance taken at the same time or about the same time. The sequence of pairs of measurements may be used for deducing a calibration function such as a calibration model and/or calibration values. At a later phase, operational phase, thorax area values which are calculated based on subsequent bio impedance measurements can be adjusted.

Using calibration function calculated based on the readings of RF sensors allows improving the accuracy and consistency of thorax area values such as fluid level values, reducing possible false negative and possible false positive alerts. In use, bio impedance devices may be used for monitoring patients hospitalized for a few days or more. During the monitoring period bio impedance measurements are collected. In some embodiments of the present invention bio impedance measurements and RF measurements are gathered for calculating calibration function. The measurements are from an area with changing fluid levels. A calibration function for adjusting subsequent bio impedance measurements taken at a later time, for instance when the patient is at home, can now be calculated to acquire improved thorax area values. The subsequent bio impedance measurements may be gathered by the same bio impedance measuring device used for capturing the bio impedance measurements or by another bio impedance measuring device. In some examples the RF sensor is integrated with the bio impedance device for example in an implantable device and the RF measurements are only triggered periodically to perform the calibration process while on a regular basis only bio impedance measurements are performed and output is calculated using the calculated calibration function. This provides for saving on energy used from a limited implanted energy source. As mentioned this method may also be used for corrections of estimates which are based on bio impedance measurements, for instance air content values and/or respiration values. Fluid content in the target thorax area, for instance the lungs includes blood content and so any other parameters based on such fluid content related bio impedance measurement can also be corrected and/or improved and/or made more accurate and/or made more quantitative using this calibration process.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference is now made to FIG. 1, which is a schematic illustration of a bio impedance measuring device 100 worn on an exemplary subject and adapted to determine target thorax area values based on a calibration function calculated according to readings of an RF sensor and readings of bio impedance measuring device, according to some embodiments of the present invention. The target thorax area values may be fluid level values (e.g. gas level and/or liquid level) in the subject's thorax 110. The bio impedance measuring device 100 may be utilized to determine a fluid level (e.g. gas and/or liquid) and/or content in the target thorax area which is intrabody thorax portion(s), thorax area(s), thorax layer(s), and/or thorax tissue(s). The bio impedance measuring device 100 includes or electronically connected to a plurality of electrodes, for example a pair of electrodes, a cathode 10 and an anode 20. The bio impedance measuring device 100 includes a processing unit 50 having one or more processors, for instance microprocessors for calculating bio impedance values and calibration function and optionally one or more RF sensors, such as 30. The one or more RF sensors may be provided in a calibration support unit, for instance with a separate processor to allow calibrating a version of the bio impedance measuring device 100 without RF sensors.

At least one of the electrodes, 10 20, the RF sensors 40 and/or the processing unit 50 are optionally housed in common housing, for instance a garment such as a vest and/or an adhesive patch. In another embodiments, the electrodes, 10 20, the RF sensors 40 and/or the processing unit 50 are divided into two housings, which are adapted to be placed in opposite sides of the body, for example frontal and posterior housings. The processing unit 50 optionally functions or operatively connected to a controller that controls timing of impedance and RF measurements. This allows correlating measurements for calculating calibration function.

The RF sensor(s) 30 may be extrabody or intrabody. For example, the RF sensor(s) 30 are integrated in a wearable garment and/or in an adhesive patch and/or implanted in the subject's body. The electrodes 10, 20 may be extrabody or intrabody. For example, electrodes are placed externally, for example integrated in a wearable garment and/or in an adhesive patch and/or implanted in the subject's body and/or integrated in a separate housing. Optionally, the RF sensor(s) 30 is divided to a receiver and a transmitter which are separated from one another. The processing unit 50 is operatively coupled to one or more of the electrodes and the RF sensor. In use, the processing unit 50 analyzes outputs of the electrodes to calculate bio impedance values of the target thorax area. This allows the processing unit 50 to determine target thorax area values such as fluid level(s), for example by adjusting bio impedance values which are captured during an operational phase based on a calibration function calculated during a learning phase.

Although FIG. 1 depicts a thorax, the bio impedance measuring device 100 may be used for monitoring any intrabody tissue, for example for post-operative monitoring, fluid injection monitoring, edema monitoring, head trauma and/or the like.

The RF sensor 40 intercepts RF radiation interacted with the monitored target thorax area. As indicated above, the RF sensor 40 or any component thereof (e.g. receiver and/or transceiver) may be positioned at various locations around the subject's body and/or implanted inside the subject's body, for instance in the thorax. Optionally, the RF sensor 40 is removably inserted into the subject's body and/or temporarily positioned at a desired location within the subject's body for acquiring RF measurements. In some implementations and scenarios the location of the RF element can be changed as desired. US Pre-Grant Publication Nos. 2010/0256462, 2013/0281800, 2011/0319,746, 2013/0060103, 2013/225989, 2014/0378813, 2015/0031979 all of which are incorporated herein by reference, disclose possible implementations of the RF sensor 40 and are examples of possible RF sensor 40 that is integrated in the herein device or method.

In a similar manner to the RF sensor 40, the processing unit 50 may be positioned outside the subject's body or be implanted inside the subject's body. The processor 50 can also be combined with or incorporated into any of the other components. Still further by way of example, the processor 50 may be implemented remotely, for example, on a computer to which the device 100 is connected via a communication network, and in such a case, the device 100 may include communication interfaces and may be operatively connected to the remote computer for remote processing of the data collected by the device 100.

In a learning phase, calibration function is optionally calculated by analyzing a sequence of pairs of measurements. The learning phase is a period during which a calibration function is calculated and/or updated. Each pair comprises bio impedance measurement and RF measurement. The learning phase may be held before the operational phase and/or during the operational phase.

Each pair includes an RF measurement and a bio impedance measurement which are correlated with one another, for instance taken at the same time or about the same time. The pairs are taken possibly during several different times when there are different thorax area values in a thorax area, for example different fluid levels in the lungs.

The sequence of pairs of measurements may be used for deducing calibration function such as a calibration function and/or a calibration model. At an operational phase, which is optionally a later phase, thorax area values are calculated by adjusting subsequent bio impedance measurements according to the calibration function. This allows obtaining absolute quantitative and/or more accurate values of fluid content.

Figure 2:
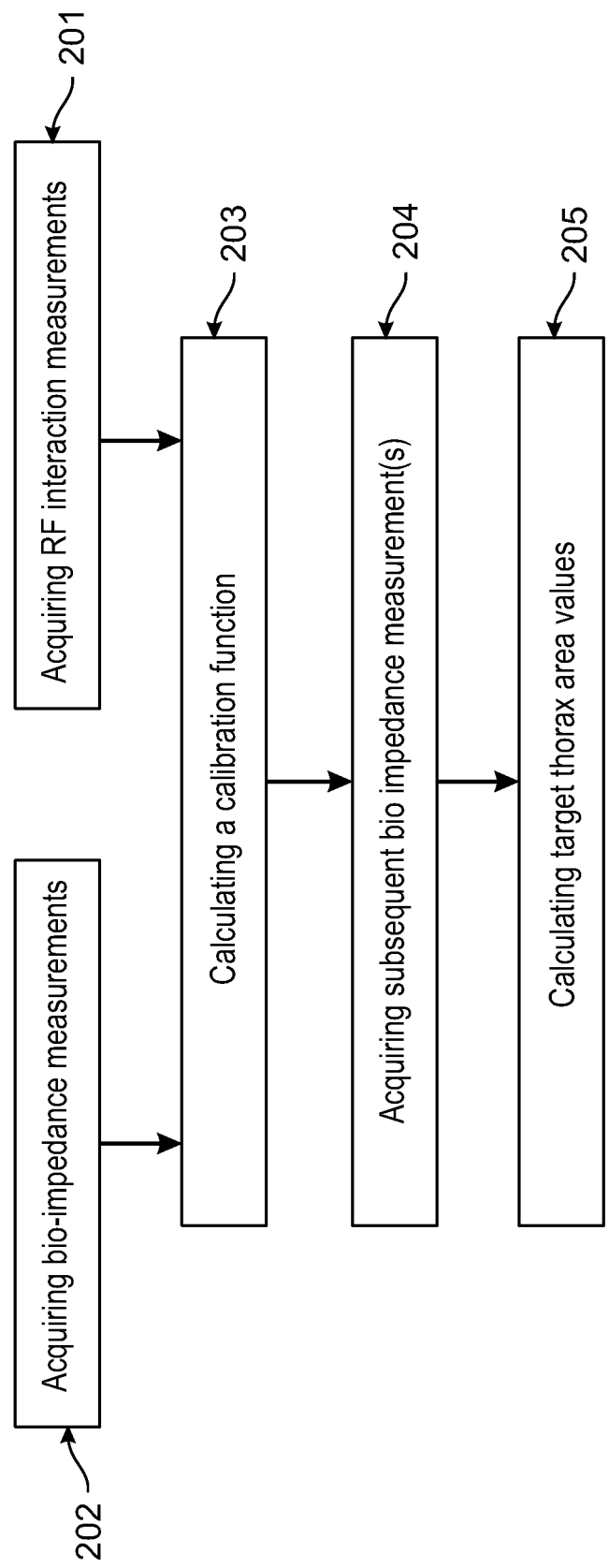
FIG. 2 is a flowchart of a method of calibrating a bio impedance measurement, optionally using the bio impedance measuring device of FIG. 1, according to some embodiments of the presently disclosed subject matter.

Reference is also made to FIG. 2 which is a flowchart 200 of a method of calibrating a bio impedance measurement, optionally using the bio impedance measuring device of FIG. 1, according to some embodiments of the presently disclosed subject matter. The method according to the presently disclosed subject matter is not necessarily limited to being implemented on this particular device and that any suitable device can be used to implement the invention.

It would be further appreciated that some examples of the present invention can be used to transform a set of measurements which include both impedance level measurements and RF interaction measurements into a calibration expression (e.g. a calibration function) which may be later used in combination with subsequent impedance level measurements to determine a fluid level in the subject's thorax at a time of the subsequent impedance level measurement. It would be noted, that one possible benefit of the proposed method is that in a case, or under circumstances where impedance level measurements fail to provide sufficiently accurate indication with regard to fluid level in the subject's thorax, a calibration phase, such as proposed according to examples of the presently disclosed subject matter, can be used to obtain greater accuracy from impedance level measurements and/or provide a quantitative absolute fluid measurement instead of a trend and/or relative measurement.

In particular, in some examples, relations and inter-relations between RF interaction measurements and impedance level measurements can be utilized to determine the calibration expression which is to be used for adjusting subsequent impedance level measurements. Various known methods have been devised which utilize two or more sets (e.g. pairs) of different types of measurements (e.g., each pair can include a RF interaction measurement and an impedance measurements) to compute a calibration expression are known in the art and can be implemented as part of examples of the presently disclosed subject matter.

During a learning phase, as shown at 201, one or more bio-impedance measurement(s) is acquired from the target thorax area, for instance by measuring electrical current using electrodes 10, 20 at a measurement time. For clarity a bio-impedance measurement may include a plurality of correlated bio-impedance measurements or an outcome of processing a plurality of correlated bio-impedance measurements (e.g. average. Mean, sum and/or the like).

Also during the learning phase, as shown at 202, an RF interaction measurement(s) are obtained from the target thorax area, for instance using the RF sensor 40. For clarity an RF interaction measurement may include a plurality of correlated RF interaction measurements or an outcome of processing a plurality of correlated RF interaction measurements (e.g. average. Mean, sum and/or the like).

Optionally, a sequence of pairs of measurements is obtained. Each pair comprises a bio impedance measurement and an RF radiation measurement which are correlated with one another, for instance taken at the same time or about the same time. The pairs are taken possibly during several different times when there are different fluid levels in the lung.

Each one of the bio-impedance measurement and the RF interaction measurement, referred to herein as pair of measurements, may be obtained at different times, for instance at proximate sequential times (e.g. with an interlude of few seconds or less therebetween) or simultaneously or at close times such that the fluid level in the lungs is the same for both measurements. The learning phase may be when the patient is treated at the hospital for example where the measurement pairs are obtained while fluid content in his lungs is changing due to the treatment. Alternatively, the learning phase may be in a period of a few minutes when the content of the lung fluid is purposefully changed for example by a breathing process, possibly guided deep breathing, leg(s) raised maneuver, a positive pressure change in a respirator, and/or when breathing into a restricted chamber, possibly while measuring the amount of air that is inhaled or exhaled.

During the learning phase, as shown at 203, a calibration function is calculated based on the one or more pairs of measurements. The calibration and the capturing of the pairs of measurements are done at a learning phase. Optionally, the calibration function is a mathematical model, for instance an equation with unknown parameters. In the calibration process these parameters are calculated to get the specific calibration function applicable for a specific patient based on RF and bio impedance measurements therefrom. Optionally, the calibration functions take into account personal parameters of the monitored patient, for instance physiological and/or anatomical parameters. Optionally, the model is a linear model, a logarithmic model, a logistic model, a sigmoid model and/or a generalized logistic function. For example, the calibration function is calculated using linear regression. In this example, a number of pairs of measurements are taken to reflect values of lungs having different lung fluid levels. For example, a simple linear model may be used by calculating $f=I+S*bimz$ where f denotes a percentage of fluid in a given space, for example air or liquid in lungs space, I and S denote Intercept and slope of Deming regression where Slope may be 1.05 and Intercept is −6.71 and bimz denotes bio impedance measurement in Ohms.

The calibration function may be calculated using preliminary tests on the collected pairs of measurements for example correlation tests or other association test to select a model. Then, a fitting process may be used to select model parameters for the calibration function. Fitting can be done via optimization methods optimizing some error function like for example root-mean-square error (RMSE) or percent of residuals or outliers.

The calibration function may be calculated based on anatomical information of the patient, for example dimensions of the thorax and/or information regarding properties of the bio impedance measuring device.

The learning phase may be held iteratively, updating the calibration function and/or upon request, for instance during resetting or initialization of the device 100. The learning phase may be repeated periodically to update the calibration function so as to allow reducing the effect of drifts and/or changes in either the physiology and/or anatomy of the patient and/or due to changes of properties of the bio impedance measurement device. The calibration allows removing or reducing the effect of drifts or changes in the bio impedance measuring device, for instance drifts or changes of the properties of the device, or the electrodes or the quality of the electrode attachment or position of their attachment locations (both in implanted or in external bio impedance devices). The calibration further allows for removing or reducing the effects of physiology or anatomy of the patient that affect the bio impedance measurement but not the lung fluid levels. For example, perspiration levels on the skin of a patient when an external bio impedance device is used.

In addition the bio impedance measuring device may ascertain from the bio impedance measurements or other internal information that a calibration process needs to be initiated.

During an operational phase, as shown at 204, subsequent bio impedance measurement(s) are acquired, optionally using the bio-impedance device 100, for instance by measuring electrical current by using the electrodes 10, 20. The operational phase is the time at which the device 100 is used for measuring target thorax area values, for instance for monitoring fluid content (e.g. blood, cellular, extracellular fluids and/or air) of the lungs of a patient. Optionally, the subsequent impedance measurement is subsequent in the sense that it is temporally removed from the time the pairs of measurements are taken. Optionally, at the time which the subsequent impedance measurement(s) is taken no RF interaction measurement is taken.

As shown at 205, a target thorax area value is now calculated by adjusting the subsequent bio impedance measurement(s) according to the calibration function. The target thorax area value is optionally a fluid level in the subject's thorax at the time of the subsequent impedance level measurement.

In one example, multiple subsequent impedance level measurements are obtained, and a relation between two or more subsequent impedance measurements is utilized in the adjusting of subsequent bio impedance measurement(s) for the computation of the thorax area value.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant methods and devices will be developed and the scope of the term a processor, a sensor, a transmitter and a receiver is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system, comprising:
  a plurality of electrodes that measure bio impedance measurements using electrical currents passing between said plurality of electrodes in a target thorax area of a target, during a learning phase;
  at least one radiofrequency (RF) sensor that measures RF radiation interaction measurements with said target thorax area during said learning phase;
  at least one processor executing code comprising code instructions to:
    time correlate said bio impedance measurements, measured during said learning phase, with said RF radiation interaction measurements, measured during said learning phase, which are taken at the same time or about the same time, calculate a calibration function based on said time correlated bio impedance measurements, measured during said learning phase and on said RF radiation interaction measurements, measured during said learning phase, adapting the calibration function used for adjusting subsequent bio impedance measurements using electric current passing between said plurality of electrodes according to at least one anatomical dimension of the target thorax area, and determine a target thorax area value by conducting the subsequent bio impedance measurements using subsequent electrical currents passing in said target thorax area during an operational phase and adjusting said subsequent bio impedance measurements using said adapted calibration function.

2. The system of claim 1, wherein said RF radiation interaction measurements and said bio impedance measurements are a sequence of pairs of time correlated measurements, each said pair comprises one of said RF radiation interaction measurements and one of said bio impedance measurements; wherein said calibration function is calculated according to said sequence of pairs.

3. The system of claim 2, wherein said pairs are taken during different times when different fluid levels are found in said target thorax area.

4. The system of claim 1, wherein said target thorax area is a lungs area.

5. The system of claim 1, wherein said calibration function is selected from a group consisting of a linear model, a logarithmic model, a logistic model, a sigmoid model and a generalized logistic function.

6. The system of claim 1, wherein said calibration function is further adapted according to at least one anatomical parameter of said target.

7. The system of claim 1, wherein said calibration function is further adapted according to at least one physiological parameter of said target.

8. A method of determining a target thorax area value, comprising:

time correlating bio impedance measurements, measured during a learning phase using electrical currents passing in a target thorax area, with RF radiation interaction measurements of RF radiation interacting with said target thorax area during said learning phase, which are taken at the same time or about the same time;

calculating a calibration function based on said time correlated bio impedance measurements using electrical currents passing in the target thorax area during the learning phase and on the RF radiation interaction measurements of RF radiation interacting with said target thorax area during said learning phase;

adapting the calibration function used for adjusting subsequent bio impedance measurements using electric current passing between said plurality of electrodes according to at least one anatomical dimension of the target thorax area; and determining a target thorax area value of said target thorax area according to adjusted subsequent bio impedance measurements taken using subsequent electrical currents passing in said target thorax area during an operational phase and adjusted using said adapted calibration function.

9. The system of claim 1, wherein said plurality of electrodes and said at least one radiofrequency (RF) sensor are integrated into a single implantable device.

10. The system of claim 9, wherein the RF radiation interaction measurements are triggered periodically to perform the calibration function calculation in an energy saving scheme and wherein said bio impedance measurements are performed on a regular basis.

11. The system of claim 5, wherein selecting said calibration function is performed using preliminary tests on collected pairs of bio impedance measurements and RF radiation interaction measurements, to select a model from said group.

* * * * *